United States Patent [19]

Siposs

[11] Patent Number: 4,606,365

[45] Date of Patent: Aug. 19, 1986

[54] BUOYANT BLOOD STOP VALVE

[76] Inventor: George G. Siposs, 2855 Velasco La., Costa Mesa, Calif. 92626

[21] Appl. No.: 751,309

[22] Filed: Jul. 2, 1985

[51] Int. Cl.$^4$ .................. F16K 31/22; F16K 33/00
[52] U.S. Cl. .................................. 137/433; 137/449; 137/192; 604/9; 604/236; 604/247
[58] Field of Search .............. 137/192, 202, 430, 433, 137/449; 604/9, 236, 247

[56] References Cited

U.S. PATENT DOCUMENTS

| 163,458 | 5/1875 | Chabot | 137/202 |
| 490,878 | 1/1893 | Marchand | 137/433 |
| 3,614,960 | 10/1971 | Pfrengle | 137/202 |
| 3,960,165 | 6/1976 | Holbrook et al. | 137/433 |

FOREIGN PATENT DOCUMENTS

| 5267 | 3/1893 | United Kingdom | 137/192 |
| 27612 | 12/1904 | United Kingdom | 137/433 |
| 7939 | 4/1908 | United Kingdom | 137/192 |
| 2028975 | 3/1980 | United Kingdom | 137/433 |

Primary Examiner—G. L. Walton
Attorney, Agent, or Firm—Allen A. Dicke, Jr.

[57] ABSTRACT

This buoyant blood stop valve is in the blood line to the patient to stop flow to prevent air embolism when the blood is exhausted from the oxygenator reservoir. The stop valve comprises a downwardly directed hemispherical cup next to the downwardly directed tubular inlet. The top of the cup is open to the inlet to permit free passage of air in and out of the top of the cup. The cup and inlet are formed in the upper valve body, and the lower valve body is secured thereto and faces the upper valve body. The bottom of the lower body has an outlet, and above the outlet is a circular valve seat, such as an O-ring in a recess. Above the O-ring the lower body has a curved bottom, but vanes are formed in the lower body and inwardly directed toward the outlet valve seat at the O-ring. Upper vanes adjacent the inlet are sloped toward the hemispherical cup. A ball, buoyant in blood, is positioned in the body and is guided in its upward floating position by the vanes which direct it toward the hemispherical cup and is guided in its downward, shutoff direction by the vanes in the side of the lower body. During forward, normal flow, the ball is quiescent in the hemispherical cup in the upper body.

14 Claims, 3 Drawing Figures

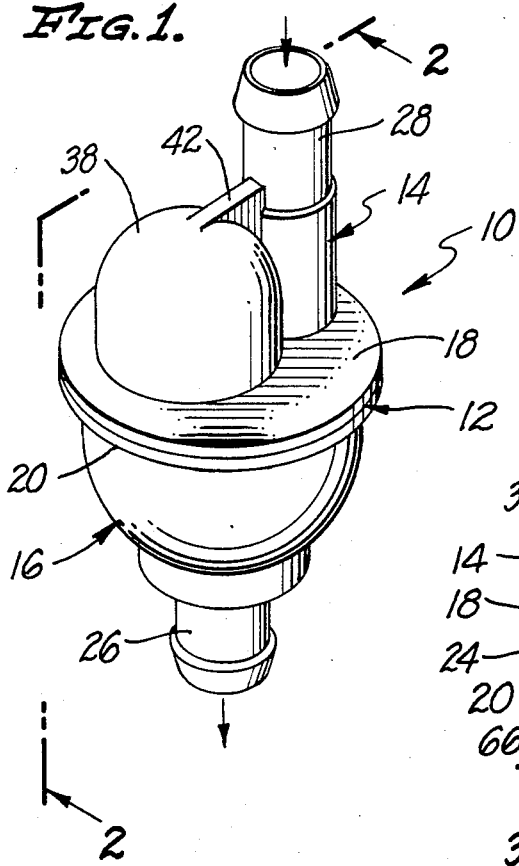
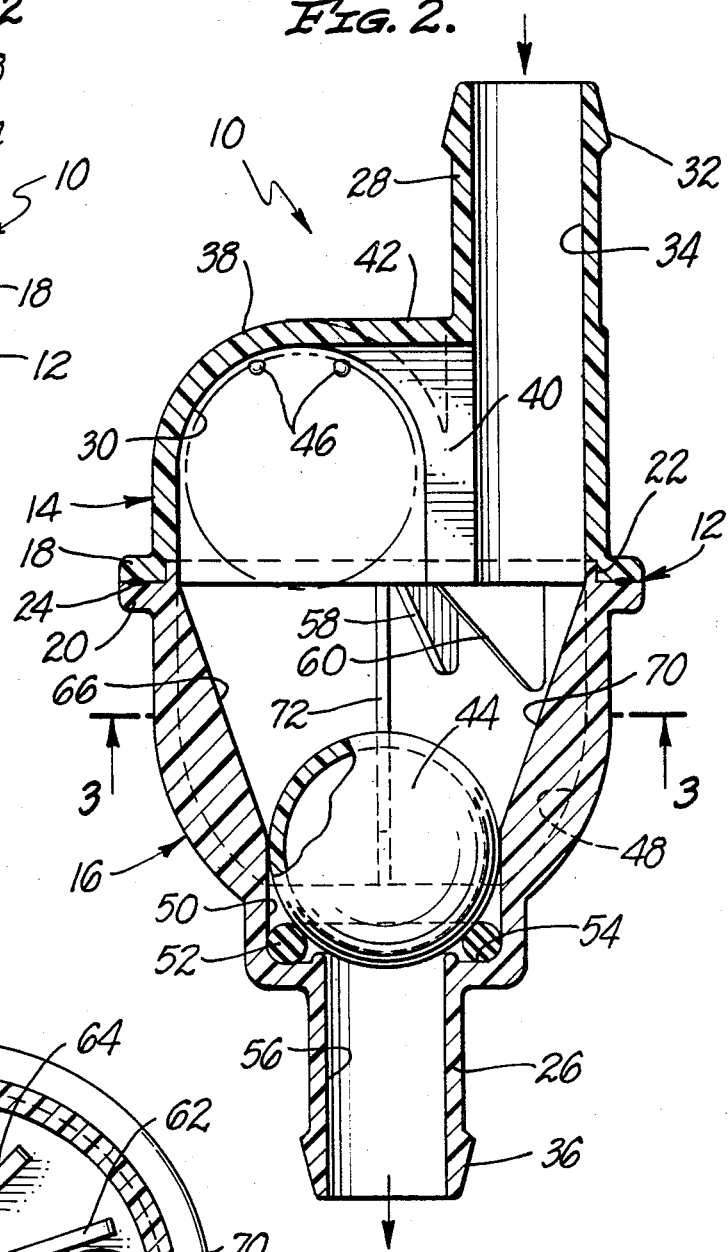
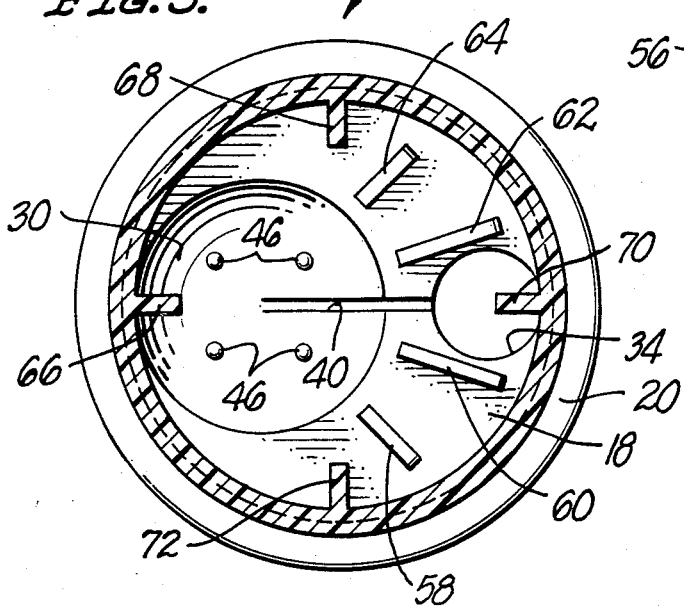

BUOYANT BLOOD STOP VALVE

BACKGROUND OF THE INVENTION

This invention is directed toward a buoyant blood stop valve which stops blood flow as blood is exhausted. The valve may also be used for cutting off other types of liquid flow when the liquid approaches exhaustion from the reservoir.

During open-heart surgery, both the heart and lungs are bypassed with an extra-corporeal circuit which includes a pump and an oxygenator. In a hard-shell oxygenator, oxygen is bubbled through the blood, and the displaced carbon dioxide escapes from the blood. The oxygenated arterial blood is filtered and returned to the body. Air can be inadvertently introduced into the arterial line when the reservoir contents of the hard-shell oxygenator is accidentaly emptied, such as when no more venous blood is being fed to the oxygenator, but the blood in the reservoir is being returned to the patient. The introduction of air into the arterial line can cause massive air embolism and usually death of the patient.

Thus, there is need for a valve to be positioned in the arterial line, which presents as little resistance to flow as is possible, which minimizes blood turbulence and trauma that may cause hemolysis and which closes automatically when massive air or other gas reaches the valve so that the valve shuts off before air passes into the arterial line beyond the blood stop valve. Such a valve should not have a tendency to inadvertently close during normal flow and should not require external manipulation or separate sensors or signals to actuate the valve. Such a valve should be pre-sterilizable and inexpensively producible.

SUMMARY OF THE INVENTION

In order to aid in the understanding of this invention, it can be stated in essentially summary form that it is directed to a buoyant blood-stop valve having a body with a top blood inlet and a bottom blood outlet. A ball, buoyant in blood, is free within the body. Next to the inlet is a downwardly open cup, sized to receive the ball and structured to guide the ball up into the cup when the ball is floating. An upwardly directed valve seat connected to the outlet receives the ball if blood level decreases, to cut off outlet flow. The valve can be used with other liquids.

It is a purpose and object of this invention to provide an automatic blood stop valve which shuts off blood flow when gross air enters the body of the stop valve in order to prevent the air from passing into a line connected to the outlet of the stop valve to automatically cut off blood flow when the blood source is depleted.

It is another purpose and object of this invention to provide a buoyant blood stop valve which presents as little resistance to flow as possible when the valve is flowing full of blood and to minimize turbulence and blood trauma that may cause hemolysis to the blood as consequence of employment of the blood stop valve.

It is a further object and advantage of the buoyant blood stop valve of this invention to automatically operate to close the stop valve upon the depletion of the blood supply without external manipulation to actuate the valve and without the requirement for other sensors or power supply.

It is another object of this invention to provide a blood stop valve which is inexpensively mass producible, compatible with blood, reliable and presterilizable so that it can be supplied to the place of use without need for further treatment.

It is another object of this invention to provide a buoyant stop valve which is useful to cut off the flow of other liquids, beside blood, upon their depletion.

Other objects and advantages of this invention will become apparent from a study of the following portion of the specification, the claims and the attached drawings.

BRIEF DESCRIPTION OF THE DRAWINGS

FIG. 1 is an isometric view of the buoyant blood stop valve of this invention.

FIG. 2 is an enlarged section taken generally along the line 2—2 of FIG. 1, with parts broken away.

FIG. 3 is an upward-looking sectional view as seen generally along the line 3—3 of FIG. 2.

DESCRIPTION OF THE PREFERRED EMBODIMENT

The buoyant blood stop valve of this invention is generally indicated at 10 in FIGS. 1, 2 and 3. The valve 10 has a body 12 which is formed of upper body portion 14 and lower body portion 16. The upper and lower body portions are respectively fitted with flanges 18 and 20 and interfitting guide and recess 22 so that the portions may be fit together and secured, as by adhesive or ultrasonic weld bond 24.

The valve body may be defined as having an upright axis, for convenience of description, and this axis is a generally central axis which is perpendicular to the plane of the flanges and passes generally through the center line of the lower body portion and outlet tube 26. Inlet tube 28 is offset with respect to this axis in order to make room for hemispheric cup 30 which is positioned on the other side of the axis. Inlet tube 28 is the inlet fitting to which the flexible arterial blood line is attached by slipping over the inlet tube.

In order to provide retention, inlet tube 28 can be provided with the conventional barbs, or more preferably has one or more annular beads 32. These beads may be rounded, as shown in FIG. 2, or may be more sharply defined as, for example, a 90° to 120° total included angle annular serration. These beads are sufficiently large to retain the arterial blood line thereon without the need for a clamp, but have a sufficiently large angle away from the end of the tube so that the tube can be pulled from the mold after the core pin which forms the inlet passage 34 is pulled. Some injection molding materials are sufficiently elastic when warm, at the point the molding is pulled from the mold, to permit withdrawal of the bead 32. A similar bead 36 is formed on outlet tube 26.

As is seen in FIGS. 1 and 2, inlet tube 28 and dome 38 which contains hemispherical cup 30, are positioned side-by-side on the upper body portion. Both are downwardly directed. They are connected by passage 40, see FIGS. 2 and 3, which is a slot within web 42 seen in FIGS. 1 and 2. Passage 40 eliminates trapping of air within cup 30 so that the liquid level in cup 30 is the same as the liquid level within inlet passage 34. Valve ball 44 is shown in the lower, no-liquid position in FIG. 2 and is shown as being a hollow ball. Valve ball 44 is made of such material as to be buoyant in the liquid in question. A hollow aluminum ball or a solid polypropylene ball is suitable when the liquid is blood. The ball is spherical and is sized to be effective as a valve. The downwardly directed hemispherical cup 30 is sized to receive the ball with a small amount of clearance. In addition, the upper interior of the hemispherical cup 30 contains tips 46 which hold the ball slightly away from the cup surface. This is to ensure that when the valve empties, there will be no suction developed between the ball and its cup which would tend to hold the ball in the upper position. Only a small clearance is necessary, and a much larger cup might allow too much ball movement so the ball rattles during flow.

The lower body 16 is also hemispherically shaped, but with a diameter which embraces both the cup and inlet passage. The hemispherical shaped surface 48 is interrupted on the axis by circular cylinder walls 50 which define an O-ring recess which contains O-ring 52. O-ring 52 is constrained between cylindrical wall 50 and end wall 54 of the recess. Outlet tube 26 and its passage 56 extend through end wall 54. O-ring 52 is sized with respect to valve ball 44 to act as a valve seat for the valve ball. When the ball is in position on its seat, as indicated in FIG. 2, downward flow through valve 10 is prevented.

When the system is being charged with blood, the ball 44 floats thereon and rises. In order to ensure that the ball rises into its cup, four vanes or posts 58, 60, 62 and 64 are formed on flange 18 to extend downwardly therefrom into the lower body. These vanes are on opposite sides of the inlet passage 34 and have surfaces which direct the rising ball away from the inlet passage and away from the underside of flange 18 toward its cup 30. In this way, ball 44 is quickly guided into its rest position for blood flow. During emptying of the valve body, ball 44 descends toward its seat on O-ring 52. Since the surface 48 is curved, ball 44 readily goes into its seat. However, to more directly guide the ball to its seat, six ball guides 66, 68, 70 and 72 are formed on the interior of the lower body portion. These ball guides have angular interior guide surfaces which direct the ball away from the hemispherical surface of the lower body toward the center where it can be more directly acted upon by downward flowing blood, so that ball 44 with more assurance quickly seats on the outlet O-ring seat even if valve axis is off vertical. These guides also improve reliability of valve closing when the valve is installed in a not quite vertical position. between cylindrical wall 50 and end wall 54 of the recess. Outlet tube 26 and its passage 56 extend through end wall 54. O-ring 52 is sized with respect to valve ball 44 to act as a valve seat for the valve ball. When the ball is in position on its seat, as indicated in FIG. 2, downward flow through valve 10 is prevented.

When the system is being charged with blood, the ball 44 floats thereon and rises. In order to ensure that the ball rises into its cup, four vanes or posts 58, 60, 62 and 64 are formed on flange 18 to extend downwardly therefrom into the lower body. These vanes are on opposite sides of the inlet passage 34 and have surfaces which direct the rising ball away from the inlet passage and away from the underside of flange 18 toward its cup 30. In this way, ball 44 is quickly guided into its rest position for blood flow. During emptying of the valve body, ball 44 descends toward its seat on O-ring 52. Since the surface 48 is curved, ball 44 readily goes into its seat. However, to more directly guide the ball to its seat, six ball guides 66, 68, 70 and 72 are formed on the interior of the lower body portion. These ball guides have angular interior guide surfaces which direct the ball away from the hemispherical surface of the lower body toward the center where it can be more directly acted upon by downward flowing blood, so that ball 44 with more assurance quickly seats on the outlet O-ring seat even if valve axis is off vertical. These guides also improve reliability of valve closing when the valve is installed in a not quite vertical position.

The upper and lower valve body portions are preferably separately injection-molded and ultrasonically welded together. Transparent polycarbonate is a suitable material therefor. Silicone rubber is a suitable material for the O-ring, and the ball is preferably polypropylene. These materials are suitable for use with blood in an extra-corporeal blood circuit. In such a circuit, the valve 10 can be configured as shown in FIG. 2 with a ball of ¾ inch diameter to form a valve suitable for such extra-corporeal blood circuits. Configured in that way, the valve has a priming volume of only 30 milliliters and is easily primed. As seen in FIG. 2, inlet flow down through inlet passage 34 tangentially engages the hemispherical surface 48 in the lower body. This causes a clockwise circulation of blood through the lower body in addition to the downward flow from inlet to outlet. The clockwise circulation is in a direction to hold the ball 44 upward in its cup 30. This circulation prevents rattling or vibration of the ball in its cup. When the liquid-air interface comes down inlet tube 28, the air spreads out through slot 40 to fill the top of the cup as the liquid level falls. Once the ball is lowered to a point where it is out of its cup, it is engaged by the mainstream liquid flow from inlet to outlet and is swept onto the valve seat and closes the valve. Thus, the valve closes the line when there is still about 10 milliliters of liquid in the chamber in the lower body. These results are the accumulative effect of the combination of geometric shapes and sizes thus described. A smooth flow path to prevent blood trauma and minimum priming volume are achieved.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A stop valve to stop the flow in a physiological liquid line when liquid is exhausted and is followed by gas, said valve comprising:

a body, walls defining a chamber within said body, an inlet passage in the top of said body for connection to a physiological liquid reservoir and an outlet passage in the bottom of said body for connection for physiological liquid utilization so that said valve body can be oriented in a generally upright position during use;

a valve seat within said chamber adjacent said outlet from said chamber, a ball free within said chamber, said ball being sized to rest on said valve seat to prevent downward flow of gas from said inlet out through said outlet, said ball being of such density as to float on physiological liquid passing downward through said valve and sink to said valve seat when physiological liquid is substantially depleted within said chamber;

walls within said chamber defining a cup sized to receive said ball beside and away from said inlet to said chamber, said cup having a rim positioned so that when said ball is floating in physiological liquid within said chamber said ball is substantially above said rim to be out of the direct physiological liquid flow path between said inlet and said outlet, ball guides positioned within said chamber to guide said ball from said cup to said seat and vanes within said chamber to guide said ball from said seat to said cup and away from said inlet; and walls defining a slot interconnecting the top of said cup and said inlet passage to define an opening between the top of said cup and said inlet passage so that air flows through said opening and into said cup before air reaches down to said rim to cause downward motion of said ball toward said valve seat before air reaches said rim.

2. The stop valve of claim 1 wherein said ball is of such average density as to float in blood and sink in air (i.e. slightly less than 1.0 specific gravity).

3. The stop valve of claim 1 wherein said ball is of such average density as to float in blood and sink in air.

4. The stop valve of claim 1 wherein said cup is substantially hemispherical and the diameter of said hemispherical cup is slightly larger than the diameter of said ball so that said ball is not retained in said cup by local suction forces.

5. The stop valve of claim 4 wherein the bottom of said chamber around said valve seat is a portion of a hemispherical surface and said surface defining said inlet is tangent with said hemispherical surface to provide smooth, circulating (in a vertical plane) flow downward through said outlet and upward under said ball when said ball was in said cup.

6. The stop valve of claim 1 wherein the bottom of said chamber around said valve seat is a portion of a hemispherical surface and said surface defining said inlet is tangent with said hemispherical surface to provide smooth, circulating flow downward through said outlet and upward under said ball when said ball was in said cup.

7. A physiological liquid valve to stop the flow of air in a blood line comprising:
a body, walls defining a chamber within said body, walls in said body defining an inlet into said body, walls in said body defining an outlet from said body;
a valve seat in said body adjacent said outlet from said body, a ball positionable upon said valve seat to close the opening in said valve to obstruct flow of fluid downward through said valve;
said chamber in said body including a downwardly facing open bottom cup positioned beside and away from said inlet into said body, said cup being sized to freely and completely receive said ball so that said ball can be completely within said cup and be completely out of the flow path between said inlet and said outlet, the top of said cup being connected by an opening to said inlet even with the top of said cup so that when said stop valve is liquid filled with a liquid of greater density than said ball, said cup fills with liquid and said ball floats into said cup so that downward liquid flow from said inlet and out said outlet away from said ball is permitted and when liquid is depleted air flows through said opening and said ball falls to engage on said seat and stop downward flow of fluid through said valve.

8. The stop valve of claim 7 wherein said walls defining said chamber in said body include a curved wall around said valve seat, said curved wall being substantially tangent to at least one of said walls defining said inlet so that liquid curves in its flow from said inlet to said outlet and said curves produces a secondary flow upward toward said cup to aid in quiescently retaining said ball within said cup.

9. The stop valve of claim 8 wherein said chamber walls include guide means for guiding said ball in its movement through said chamber between said seat and said cup.

10. The stop valve of claim 9 wherein said guide means includes ball guides within said chamber to guide said ball in its movement from said cup to said seat.

11. The stop valve of claim 10 wherein said guide means includes a plurality of vanes, at least one positioned on each side of said inlet, to guide said ball from said seat to said cup.

12. The stop valve of claim 11 wherein said cup is larger than said ball and there are tips within said cup to hold said ball spaced from the surface of said cup to eliminate localized fluid forces which would aid in retaining said ball within said cup.

13. The stop valve of claim 9 wherein said guide means is for guiding said ball from said seat to said cup.

14. A liquid stop valve comprising:
a body, walls defining a chamber within said body, walls in said body defining an inlet into said body, walls in said body defining an outlet from said body, said chamber being oriented and connected to said inlet and outlet so that flow is downward through said chamber;
a valve seat at the bottom of said chamber in said body adjacent said outlet from said body, a ball positionable upon said valve seat to close the opening in said valve to obstruct flow of fluid downward through said valve and downward through said chamber, said ball being of less density than the liquid so said ball floats on the liquid flowing from said inlet to said outlet;
said chamber in said body including a downwardly facing open bottom cup sized to completely and freely receive said ball, said cup being positioned to receive said ball and hold it out of liquid flow from said inlet to said outlet and when liquid is depleted, said ball falls to engage on said seat and stop downward flow of fluid through said valve; and
a passage between the top of said cup and said inlet to permit limited flow between the top of said cup and said inlet so as to maintain said ball within said cup so that when liquid is depleted at said passage in said inlet, liquid flows down out of said cup permitting said ball to fall to smoothly move onto said seat.

* * * * *